(12) United States Patent
Sjostrom et al.

(10) Patent No.: US 9,044,138 B2
(45) Date of Patent: Jun. 2, 2015

(54) STEERABLE ELECTRONIC STEREOSCOPIC ENDOSCOPE

(71) Applicant: Viking Systems, Inc., Westborough, MA (US)

(72) Inventors: Douglas D. Sjostrom, Tewksbury, MA (US); Yuri Kazakevich, Newton, MA (US); William Bopp, Incline Village, NV (US)

(73) Assignee: Viking Systems, Inc., Westborough, MA (US)

( * ) Notice: Subject to any disclaimer, the term of this patent is extended or adjusted under 35 U.S.C. 154(b) by 0 days.

(21) Appl. No.: 13/657,648

(22) Filed: Oct. 22, 2012

(65) Prior Publication Data

US 2013/0102846 A1 Apr. 25, 2013

Related U.S. Application Data

(60) Provisional application No. 61/550,095, filed on Oct. 21, 2011.

(51) Int. Cl.
| | |
|---|---|
| *A61B 1/04* | (2006.01) |
| *A61B 1/00* | (2006.01) |
| *A61B 1/07* | (2006.01) |
| *A61B 1/005* | (2006.01) |
| *A61B 1/05* | (2006.01) |

(52) U.S. Cl.
CPC ............... *A61B 1/00193* (2013.01); *A61B 1/07* (2013.01); *A61B 1/0052* (2013.01); *A61B 1/0055* (2013.01); *A61B 1/05* (2013.01)

(58) Field of Classification Search
CPC ........................... A61B 1/00193; A61B 1/0052
USPC ......... 600/111, 114, 146, 139, 148, 149, 585; 606/108; 604/528, 95.01, 510; 348/65
See application file for complete search history.

(56) References Cited

U.S. PATENT DOCUMENTS

| | | | |
|---|---|---|---|
| 3,788,303 A * | 1/1974 | Hall .............................. | 600/148 |
| 4,924,852 A | 5/1990 | Suzuki et al. | |
| 5,007,406 A * | 4/1991 | Takahashi et al. ............ | 600/119 |
| 5,329,887 A * | 7/1994 | Ailinger et al. ............... | 600/148 |
| 5,464,007 A * | 11/1995 | Krauter et al. ................ | 600/144 |
| 5,496,260 A * | 3/1996 | Krauter et al. ................ | 600/148 |
| 5,575,755 A * | 11/1996 | Krauter et al. ................ | 600/148 |
| 5,846,183 A * | 12/1998 | Chilcoat ....................... | 600/136 |
| 6,080,101 A | 6/2000 | Tatsuno et al. | |
| 6,547,721 B1 * | 4/2003 | Higuma et al. ............... | 600/133 |
| 6,923,758 B2 * | 8/2005 | Ishibiki ........................ | 600/133 |
| 7,491,165 B2 * | 2/2009 | Kogasaka et al. ............ | 600/104 |
| 7,731,072 B2 * | 6/2010 | Timm et al. ................. | 227/175.1 |
| 7,833,156 B2 * | 11/2010 | Williams et al. .............. | 600/184 |
| 8,029,531 B2 * | 10/2011 | Lee et al. ...................... | 606/205 |
| 8,100,824 B2 * | 1/2012 | Hegeman et al. ............. | 600/141 |
| RE43,281 E * | 3/2012 | Higuma et al. ............... | 600/133 |
| 8,287,448 B2 * | 10/2012 | Schaaf .......................... | 600/146 |
| 8,287,449 B2 * | 10/2012 | Tanaka .......................... | 600/149 |
| 8,363,097 B2 * | 1/2013 | Kazakevich et al. .......... | 348/68 |
| 8,409,175 B2 * | 4/2013 | Lee et al. .......................... | 606/1 |

(Continued)

*Primary Examiner* — John P Leubecker
*Assistant Examiner* — Ronald D Colque
(74) *Attorney, Agent, or Firm* — Pandiscio & Pandiscio

(57) ABSTRACT

A steerable stereoscopic endoscope including a shaft having a distal end, a proximal end, and an articulating region therebetween; a stereo image acquisition mechanism disposed at the distal end of the shaft for acquiring stereo images of a remote site; and a mechanism for steering the portion of the shaft distal to the articulating region.

32 Claims, 18 Drawing Sheets

(56) References Cited

U.S. PATENT DOCUMENTS

| | | | |
|---|---|---|---|
| 8,444,547 B2* | 5/2013 | Miyamoto et al. | 600/104 |
| 8,518,024 B2* | 8/2013 | Williams et al. | 606/1 |
| 8,556,805 B2* | 10/2013 | Hashimoto et al. | 600/145 |
| 8,617,054 B2* | 12/2013 | Miyamoto et al. | 600/106 |
| 8,708,891 B2* | 4/2014 | Sjostrom et al. | 600/111 |
| 2003/0149339 A1* | 8/2003 | Ishibiki | 600/160 |
| 2004/0111012 A1* | 6/2004 | Whitman | 600/179 |
| 2004/0225183 A1* | 11/2004 | Michlitsch et al. | 600/106 |
| 2005/0137456 A1* | 6/2005 | Saadat et al. | 600/114 |
| 2006/0009678 A1* | 1/2006 | Jaffe et al. | 600/114 |
| 2006/0167416 A1* | 7/2006 | Mathis et al. | 604/164.01 |
| 2006/0178562 A1* | 8/2006 | Saadat et al. | 600/142 |
| 2007/0112250 A1* | 5/2007 | Kura et al. | 600/114 |
| 2007/0167679 A1* | 7/2007 | Miyamoto et al. | 600/106 |
| 2007/0167680 A1* | 7/2007 | Miyamoto et al. | 600/106 |
| 2007/0221700 A1* | 9/2007 | Ortiz et al. | 227/175.1 |
| 2007/0221701 A1* | 9/2007 | Ortiz et al. | 227/175.1 |
| 2007/0250110 A1* | 10/2007 | Lu et al. | 606/205 |
| 2007/0276430 A1* | 11/2007 | Lee et al. | 606/205 |
| 2007/0299387 A1* | 12/2007 | Williams et al. | 604/22 |
| 2008/0045803 A1* | 2/2008 | Williams et al. | 600/204 |
| 2008/0051631 A1* | 2/2008 | Dejima et al. | 600/114 |
| 2008/0188868 A1* | 8/2008 | Weitzner et al. | 606/130 |
| 2008/0188869 A1* | 8/2008 | Weitzner et al. | 606/130 |
| 2008/0188890 A1* | 8/2008 | Weitzner et al. | 606/205 |
| 2008/0221391 A1* | 9/2008 | Weitzner et al. | 600/118 |
| 2008/0234547 A1* | 9/2008 | Irion et al. | 600/133 |
| 2008/0243176 A1* | 10/2008 | Weitzner et al. | 606/206 |
| 2008/0255420 A1* | 10/2008 | Lee et al. | 600/137 |
| 2008/0262294 A1* | 10/2008 | Ewers et al. | 600/104 |
| 2008/0262300 A1* | 10/2008 | Ewers et al. | 600/114 |
| 2008/0269561 A1 | 10/2008 | Banik et al. | |
| 2008/0287862 A1* | 11/2008 | Weitzner et al. | 604/28 |
| 2008/0287963 A1* | 11/2008 | Rogers et al. | 606/130 |
| 2009/0069842 A1* | 3/2009 | Lee et al. | 606/205 |
| 2009/0076329 A1 | 3/2009 | Su et al. | |
| 2009/0171161 A1* | 7/2009 | Ewers et al. | 600/149 |
| 2009/0209820 A1* | 8/2009 | Tanaka | 600/149 |
| 2009/0253961 A1* | 10/2009 | Le et al. | 600/121 |
| 2010/0030018 A1* | 2/2010 | Fortier et al. | 600/104 |
| 2010/0049000 A2* | 2/2010 | Tanaka | 600/149 |
| 2010/0099949 A1* | 4/2010 | Tilson et al. | 600/116 |
| 2010/0198016 A1* | 8/2010 | Tilson et al. | 600/139 |
| 2010/0211086 A1* | 8/2010 | Ewers et al. | 606/153 |
| 2010/0249497 A1* | 9/2010 | Peine et al. | 600/104 |
| 2010/0261961 A1* | 10/2010 | Scott et al. | 600/111 |
| 2010/0286480 A1* | 11/2010 | Peine et al. | 600/131 |
| 2011/0009694 A1* | 1/2011 | Schultz et al. | 600/109 |
| 2011/0060186 A1* | 3/2011 | Tilson et al. | 600/104 |
| 2011/0196199 A1 | 8/2011 | Donhowe et al. | |
| 2011/0230723 A1* | 9/2011 | Castro et al. | 600/205 |
| 2011/0306836 A1* | 12/2011 | Ohline et al. | 600/146 |
| 2012/0041266 A1* | 2/2012 | Buehs | 600/142 |

* cited by examiner

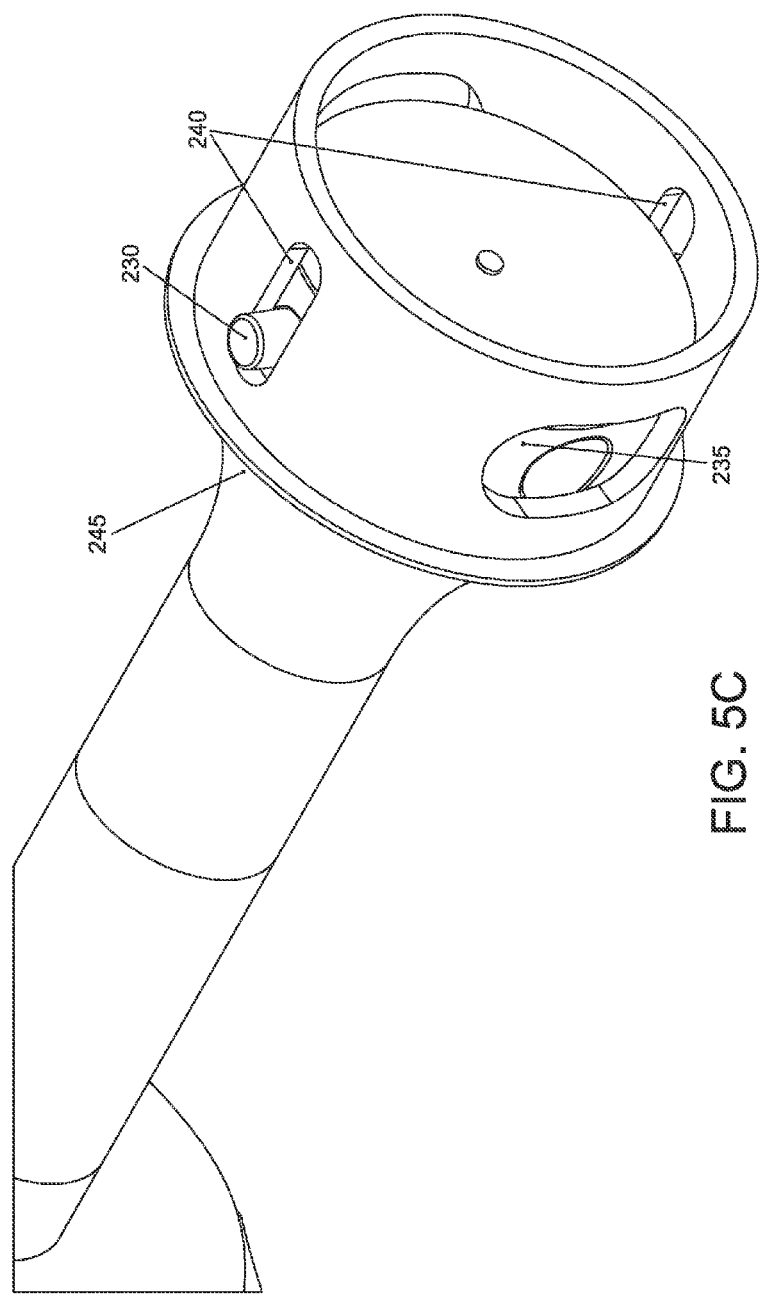

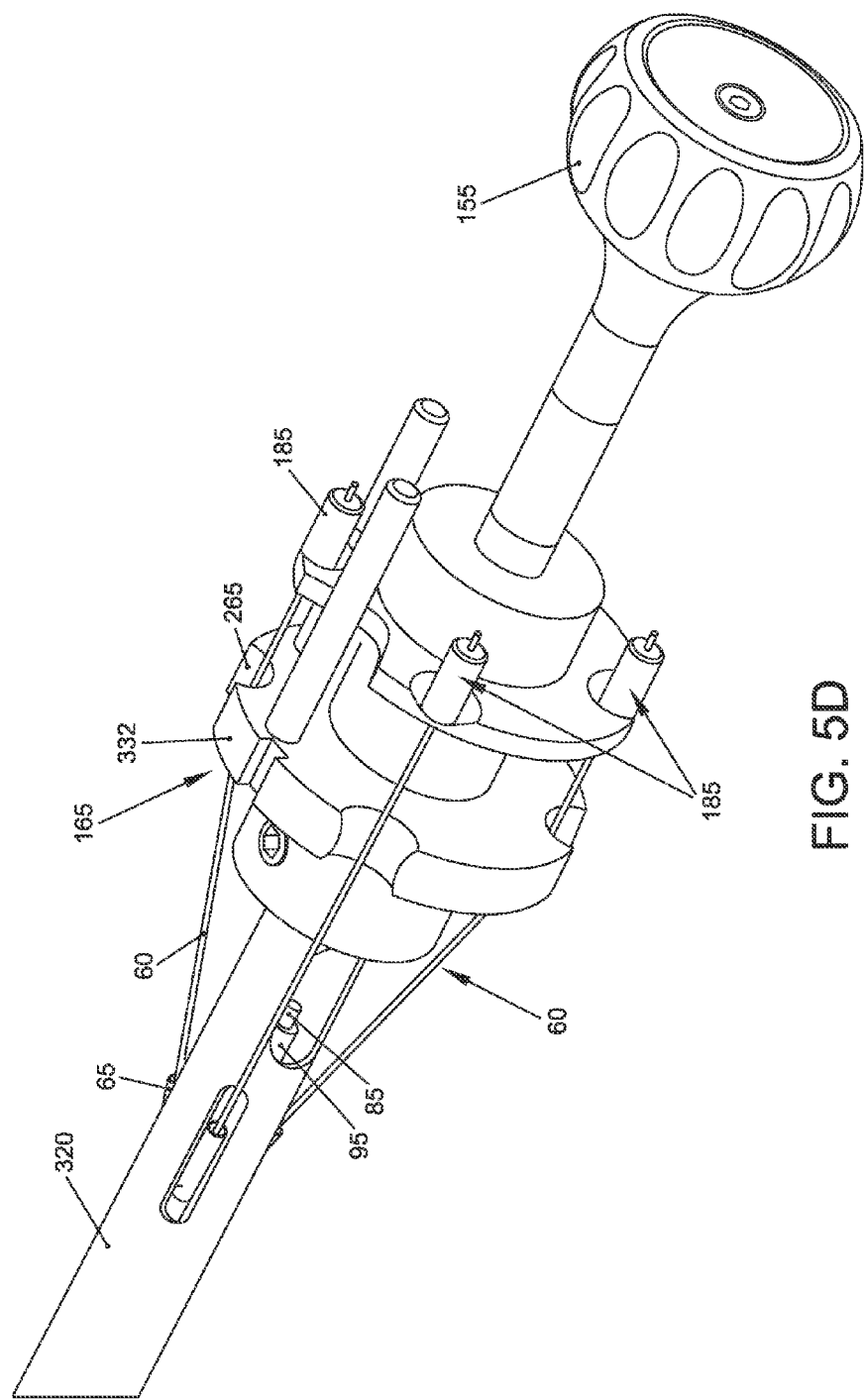

STEERABLE ELECTRONIC STEREOSCOPIC ENDOSCOPE

REFERENCE TO PENDING PRIOR PATENT APPLICATION

This patent application claims benefit of U.S. Provisional Patent Application Ser. No. 61/550,095, filed Oct. 21, 2011 by Douglas D. Sjostrom et al. for STEERABLE STEREOSCOPIC ELECTRONIC ENDOSCOPE, which patent application is hereby incorporated herein by reference.

FIELD OF THE INVENTION

This invention relates to visualization systems in general, and more particularly to stereoscopic endoscopes which may be articulated and directed by the user.

BACKGROUND OF THE INVENTION

Typically endoscopes that may be articulated are limited to single channel optical or electronic image transmission means.

Optical endoscopes that are flexible currently rely upon coherent optical fiber bundles to transmit coarsely pixilated images, giving the user the impression of viewing a scene through a grid, not unlike viewing a scene through a window screen.

Electronic endoscopes (also known as "chip-on-tip" or "chip-on-stick" endoscopes) that are flexible feature a single, highly miniaturized image sensor disposed at the distal end of the device.

Both types of endoscopes (i.e., optical and electronic) typically include fiber optic illumination means for illuminating the operative field which is being directly visualized.

Due to challenges in adequately sealing flexible and articulating endoscopes, these types of devices are limited to cold sterilization techniques. Typically such flexible and articulating endoscopes are hand-held and steered directly by the user.

Stereoscopic (i.e., 3D) endoscopes differ from their non-stereo counterparts in that they are more sensitive to optical misalignments. Not only must each channel be optically aligned for the best image, but also key optical parameters for each channel (such as magnification, bore-sight, image rotation, image focus, etc.) must be identical between the two channels—otherwise, an unwanted parallax will be created in the system, causing depth distortions and user eye strain/fatigue in converging the two images.

DESCRIPTION OF THE INVENTION

The present invention addresses the forgoing issues and provides a steerable electronic stereoscopic endoscope which appropriately maintains channel alignment, and which appropriately maintains key optical parameters for each channel, so as to avoid unwanted parallax and thus minimize user eye strain/fatigue. In addition, the steerable electronic stereoscopic endoscope of the present invention is able to withstand the pressure and elevated temperatures of steam autoclave sterilization, so that the steerable electronic stereoscopic endoscope may be sterilized with both hot and cold sterilization techniques.

In one preferred form of the invention, there is provided a steerable stereoscopic endoscope comprising:

a shaft having a distal end, a proximal end, and an articulating region therebetween;

stereo image acquisition means disposed at the distal end of the shaft for acquiring stereo images of a remote site; and means for steering the portion of the shaft distal to the articulating region.

In another preferred form of the invention, there is provided a steerable endoscope comprising:

a shaft having a distal end, a proximal end, and an articulating region therebetween; and image acquisition means disposed at the distal end of the shaft for acquiring an image of a remote site;

wherein the distal end of the shaft comprises at least two decks sealably connected by flexible metal bellows.

In another preferred form of the invention, there is provided a steerable endoscope comprising:

a shaft having a distal end, a proximal end, and an articulating region therebetween; and image acquisition means disposed at the distal end of the shaft for acquiring an image of a remote site;

wherein the distal end of the shaft comprises a wire spine having a distal end and a proximal end, a first deck mounted to the distal end of the wire spine and a second deck mounted to the proximal end of the wire spine.

In another preferred form of the invention, there is provided a steerable endoscope comprising:

a shaft having a distal end, a proximal end, and an articulating region therebetween;

image acquisition means disposed at the distal end of the shaft for acquiring an image of a remote site;

a steering and brake assembly mounted to the proximal end of the shaft; and a plurality of actuating wires extending between the distal end of the shaft and the steering and brake assembly;

wherein the steering and brake assembly comprises:

a base having a spherical seat;

a bearing ball rotatably mounted within the spherical seat of the base;

a joystick core mounted to the ball;

a swash plate mounted to the joystick core, wherein the plurality of actuating wires are attached to the swash plate;

a brake for selectively locking the bearing ball in position within the spherical seat of the base; and means for actuating the brake.

In another preferred form of the invention, there is provided a steerable endoscope comprising:

a shaft having a distal end, a proximal end, and an articulating region therebetween;

image acquisition means disposed at the distal end of the shaft for acquiring an image of a remote site; and a control joystick for steering the portion of the shaft distal to the articulating region.

In another preferred form of the invention, there is provided a method for acquiring an image of a remote site, the method comprising:

providing a steerable stereoscopic endoscope comprising:

a shaft having a distal end, a proximal end, and an articulating region therebetween;

stereo image acquisition means disposed at the distal end of the shaft for acquiring stereo images of a remote site; and means for steering the portion of the shaft distal to the articulating region; and using the steerable stereoscopic endoscope to acquire an image of a remote site.

In another preferred form of the invention, there is provided a method for acquiring an image of a remote site, the method comprising:

providing a steerable endoscope comprising:
a shaft having a distal end, a proximal end, and an articulating region therebetween; and
image acquisition means disposed at the distal end of the shaft for acquiring an image of a remote site;
wherein the distal end of the shaft comprises at least two decks sealably connected by flexible metal bellows; and
using the steerable endoscope to acquire an image of a remote site.

In another preferred form of the invention, there is provided a method for acquiring an image of a remote site, the method comprising:
providing a steerable endoscope comprising:
a shaft having a distal end, a proximal end, and an articulating region therebetween; and
image acquisition means disposed at the distal end of the shaft for acquiring an image of a remote site;
wherein the distal end of the shaft comprises a wire spine having a distal end and a proximal end, a first deck mounted to the distal end of the wire spine and a second deck mounted to the proximal end of the wire spine; and
using the steerable endoscope to acquire an image of a remote site.

In another preferred form of the invention, there is provided a method for acquiring an image of a remote site, the method comprising:
providing a steerable endoscope comprising:
a shaft having a distal end, a proximal end, and an articulating region therebetween;
image acquisition means disposed at the distal end of the shaft for acquiring an image of a remote site;
a steering and brake assembly mounted to the proximal end of the shaft; and
a plurality of actuating wires extending between the distal end of the shaft and the steering and brake assembly;
wherein the steering and brake assembly comprises:
a base having a spherical seat;
a bearing ball rotatably mounted within the spherical seat of the base;
a joystick core mounted to the ball;
a swash plate mounted to the joystick core, wherein the plurality of actuating wires are attached to the swash plate;
a brake for selectively locking the bearing ball in position within the spherical seat of the base; and
means for actuating the brake; and
using the steerable endoscope to acquire an image of a remote site.

In another preferred form of the invention, there is provided a method for acquiring an image of a remote site, the method comprising:
providing a steerable endoscope comprising:
a shaft having a distal end, a proximal end, and an articulating region therebetween;
image acquisition means disposed at the distal end of the shaft for acquiring an image of a remote site; and
a control joystick for steering the portion of the shaft distal to the articulating region; and
using the steerable endoscope to acquire an image of a remote site.

In another preferred form of the invention, there is provided a steerable endoscope comprising:
a shaft having a distal end, a proximal end, and an articulating region therebetween;
image acquisition means disposed at the distal end of the shaft for acquiring an image of a remote site; and
means for steering the portion of the shaft distal to the articulating region;
wherein the image acquisition means are isolated within a capsule configured to protect the image acquisition means against multiple steam autoclave cycles.

In another preferred form of the invention, there is provided a method for acquiring an image of a remote site, the method comprising:
providing a steerable endoscope comprising:
a shaft having a distal end, a proximal end, and an articulating region therebetween;
image acquisition means disposed at the distal end of the shaft for acquiring an image of a remote site; and
means for steering the portion of the shaft distal to the articulating region;
wherein the image acquisition means are isolated within a capsule configured to protect the image acquisition means against multiple steam autoclave cycles; and
using the steerable endoscope to acquire an image of a remote site.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 5, 5A, 5B, 5C, 5D and 5E are schematic views showing the endoscope's steering and brake assembly and details thereof;

DETAILED DESCRIPTION OF THE PREFERRED EMBODIMENTS

Figure 1:
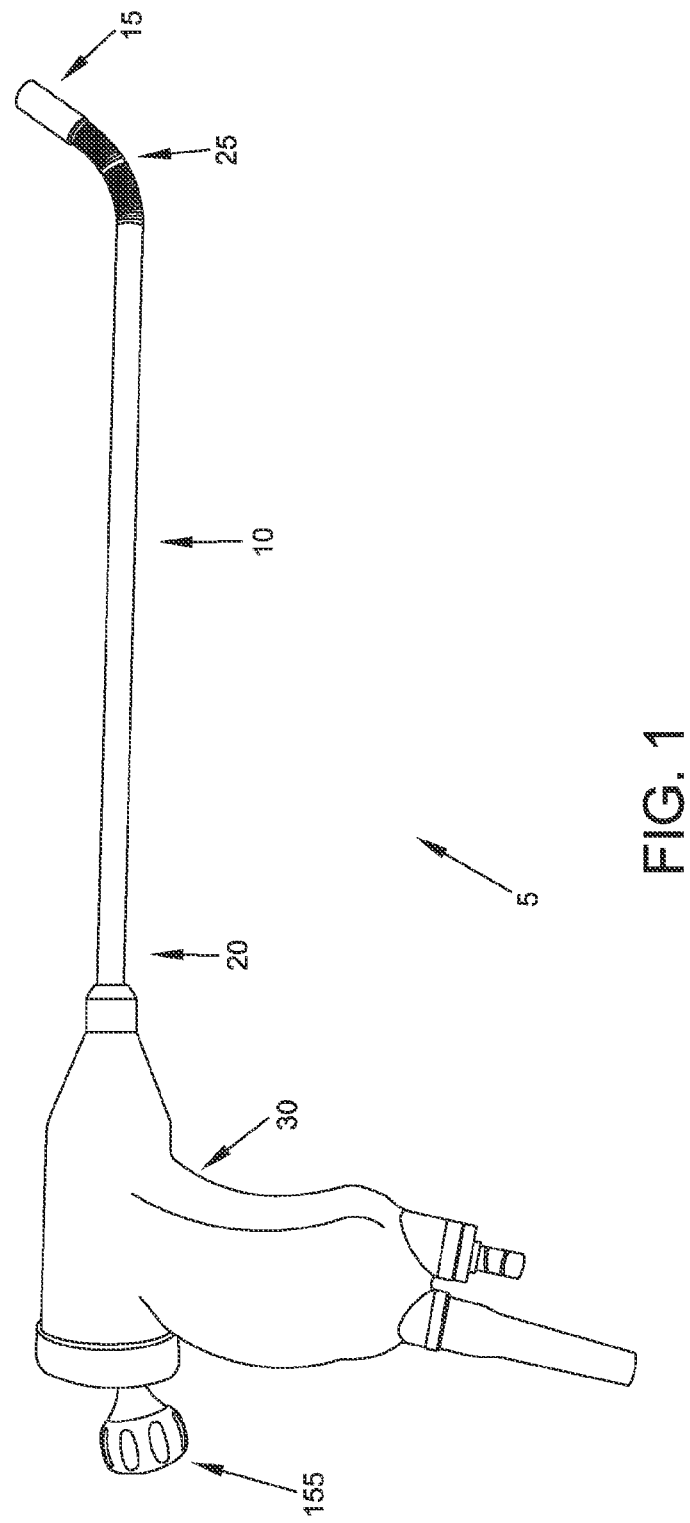
FIG. 1 is a schematic view showing a steerable electronic stereoscopic endoscope formed in accordance with the present invention.

Looking first at FIG. 1, there is shown a steerable electronic stereoscopic endoscope 5 formed in accordance with the present invention. Endoscope 5 generally comprises a shaft 10 having a distal end 15 and a proximal end 20. Shaft 10 is flexible in the articulating region 25 as will hereinafter be discussed in further detail. The proximal end 20 of shaft 10 is mounted to a handle 30.

Figure 2:
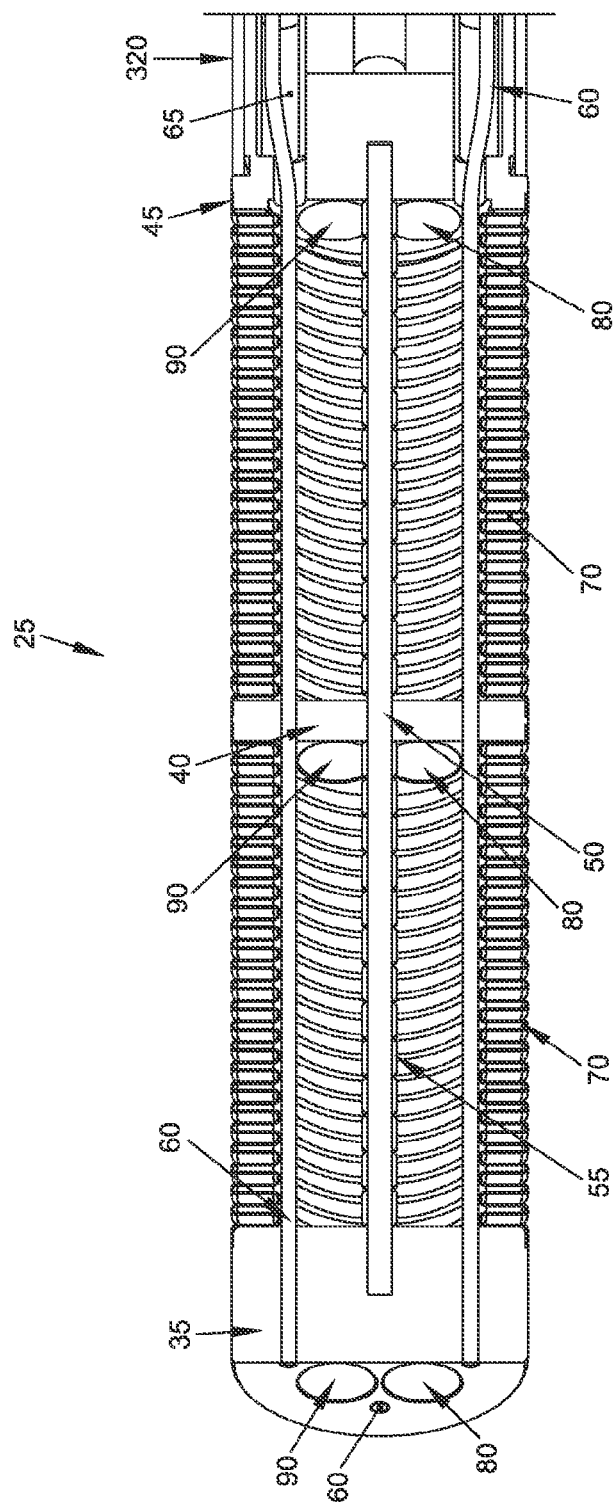
FIGS. 2 and 2A are schematic views showing the articulating region of the shaft of the endoscope.

FIG. 2 shows shaft 10 in the articulating region 25. Articulating region 25 generally comprises a distal joiner deck 35, at least one intermediate deck 40 and a base joiner deck 45. Further elements in the articulating region 25 include a central supporting Nitinol super-elastic wire 50 captively supported within distal joiner deck 35 and base joiner deck 45. Intermediate deck 40 is slidably supported by Nitinol super-elastic wire 50. A plurality of stacked spacer elements (e.g., rings) 55 are coaxially mounted on Nitinol superelastic wire 50 between distal joiner deck 35 and the at least one intermediate deck 40, and between the at least one intermediate deck 40 and base joiner deck 45, so as to ensure a fixed spacing between distal joiner deck 35 and the at least one intermediate deck 40, and between the at least one intermediate deck 40 and base joiner deck 45, regardless of endoscope articulation.

Four actuating wires 60 (only three of which are seen in FIG. 2) are bonded securely within distal joiner deck 35 and slidably pass through the at least one intermediate deck 40 and base joiner deck 45. Four conduit tubes 65, joined to base joiner deck 45 and extending proximally therefrom, maintain straightness and proper orientation of actuating wires 60 as the actuating wires pass through the axial length of endoscope 5.

Figure 2A:
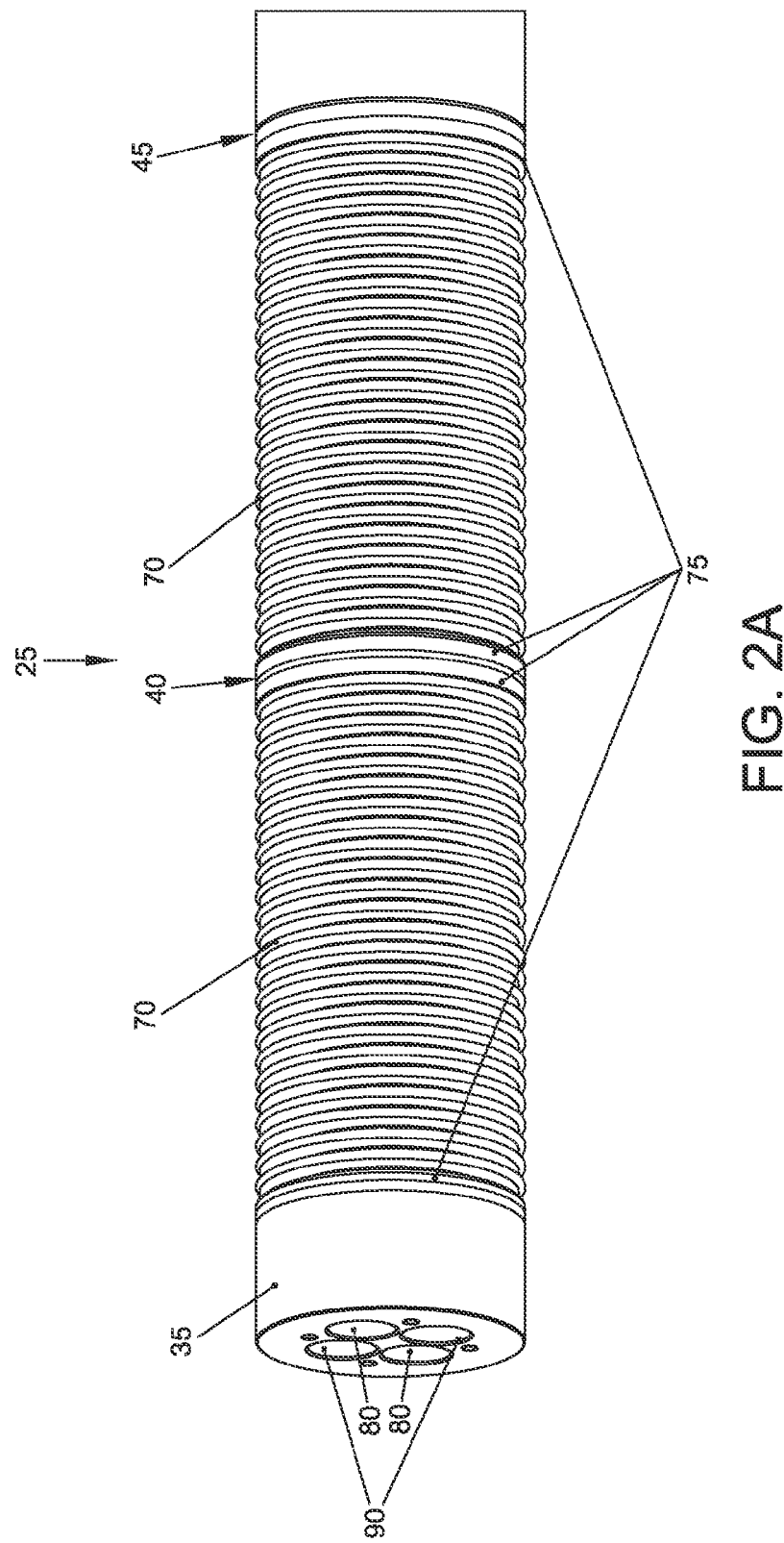

Looking now at FIGS. 2 and 2A, two metal bellows 70 are hermetically joined (at joints 75) to their respective decks 35 and 40, and 40 and 45, providing rotational rigidity to endoscope 5 and hermetically sealing the elements within.

Holes 80 in decks 35, 40 and 45 allow electronic leads 85 (see FIG. 3) to slide freely within decks 35, 40 and 45, and holes 90 in decks 35, 40 and 45 allow fiber optic illumination bundles 95 (see FIG. 3) to slide freely within decks 35, 40 and 45 during endoscope articulation.

Figure 3:
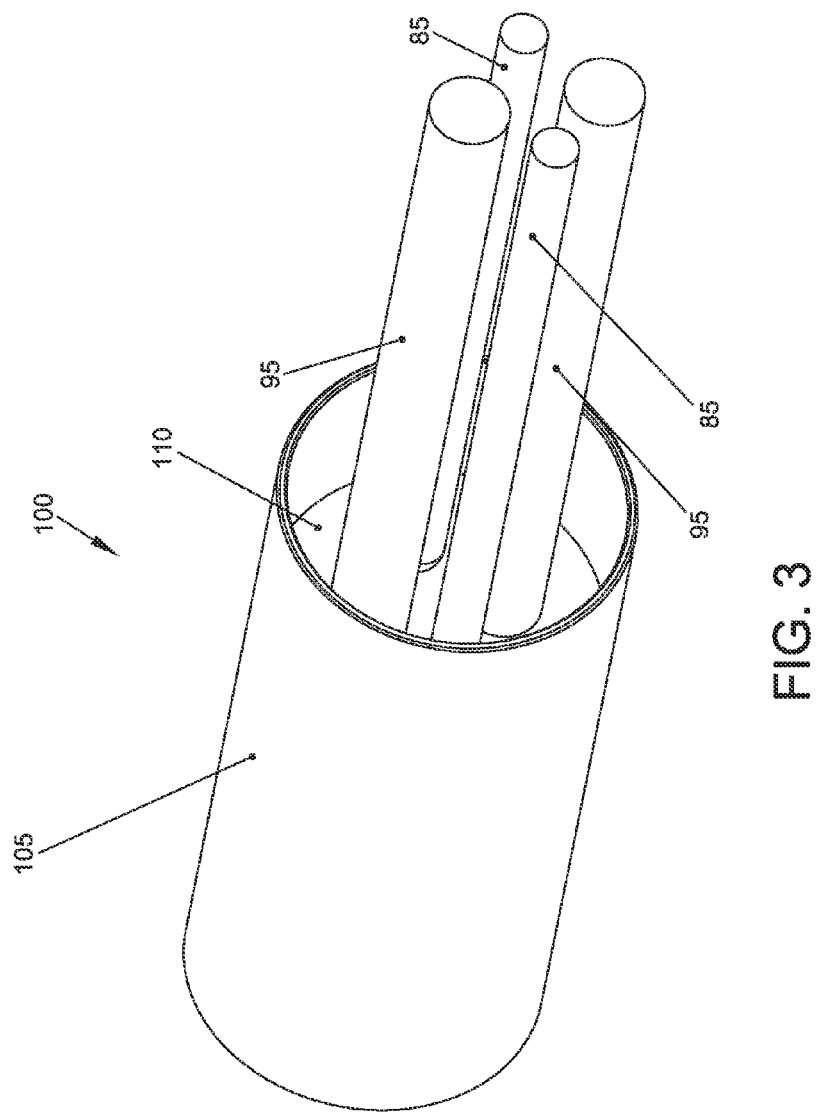
FIGS. 3, 3A, 3B and 3C are schematic views showing the endoscope's sealed camera module and details thereof.

FIG. 3 shows the sealed camera module 100 which is disposed in shaft 10 distal to distal joiner deck 35, with electronic leads 85 and fiber optic illumination bundles 95 passing through holes 80 and 90 within decks 35, 40 and 45. Sealed camera module 100 comprises an outer sleeve 105, an elastomer seal 110 and the aforementioned electronic leads 85 (from the camera module's image sensor assemblies, see below) and optical fiber illumination bundles 95.

Figure 3A:
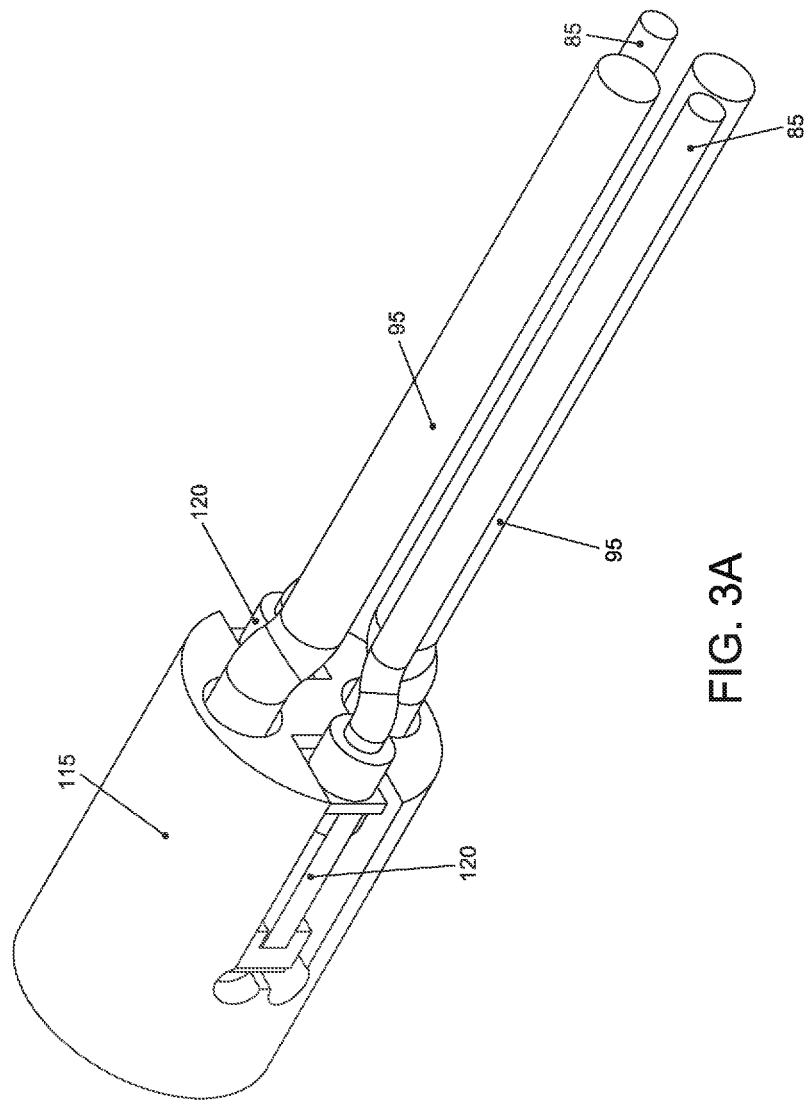
Figure 3B:
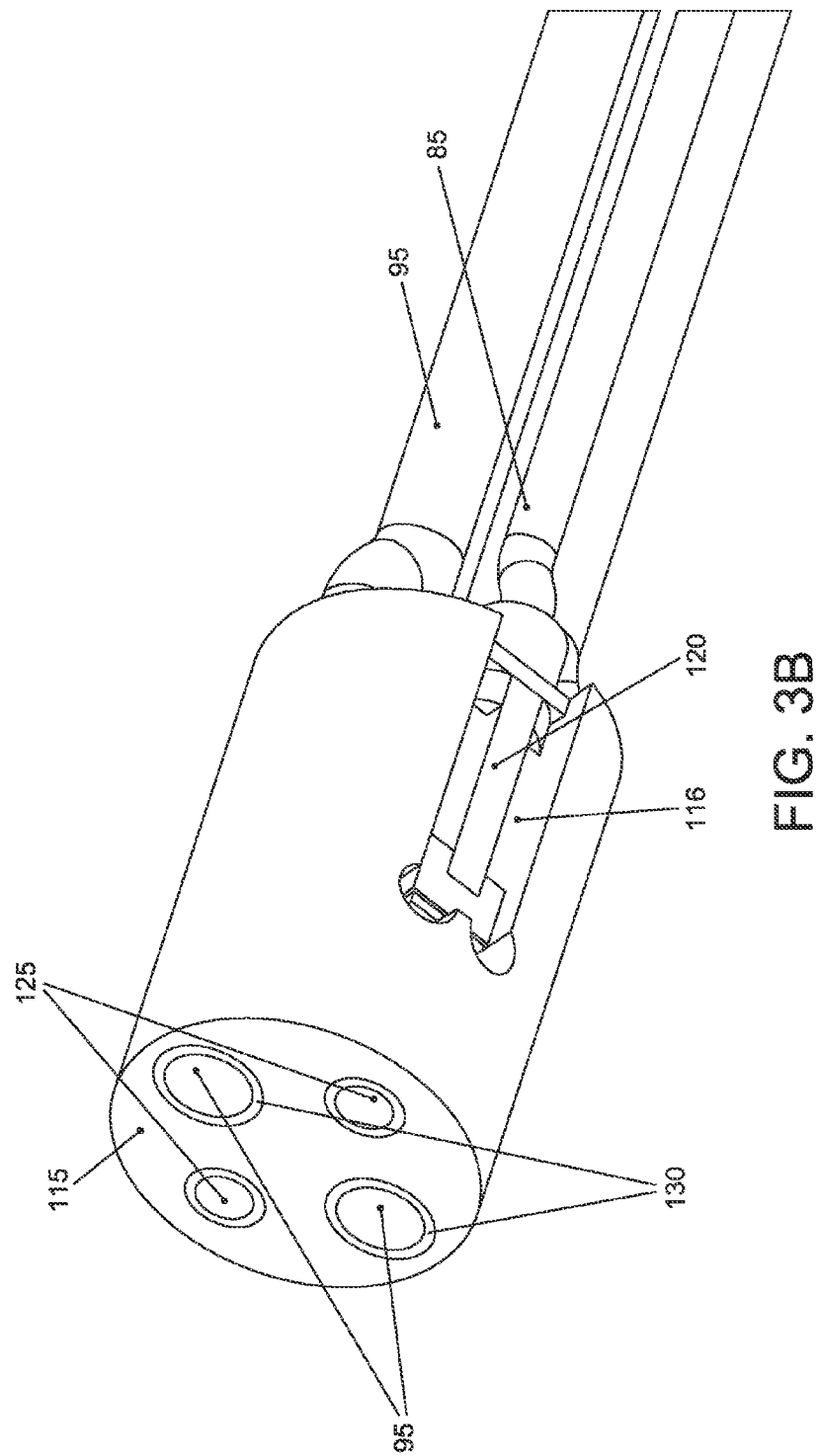
Figure 3C:
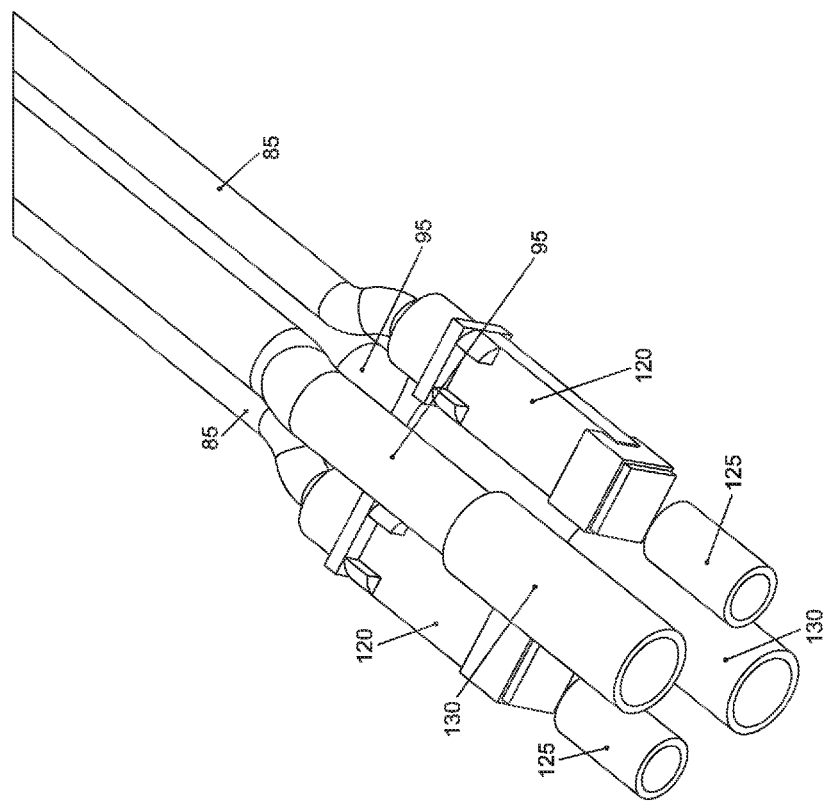

FIGS. 3A, 3B and 3C show interior construction details of sealed camera module 100.

FIG. 3A shows the module body 115 which is disposed coaxially within outer sleeve 105 of sealed camera module 100, and an image sensor assembly 120, as well as the aforementioned electronic leads 85 and fiber optic illumination bundles 95.

FIG. 3C illustrates the interior elements of sealed camera module 100 aligned and bonded within module body 115. Shown are pairs of CCD image sensor assemblies 120, camera lens cells 125 and optical fiber illumination bundles 95 bonded and polished within ferrules 130.

FIG. 3B illustrates the foregoing elements bonded within module body 115. The pair of image sensor assemblies 120 are carefully optically aligned and then bonded (e.g., at 116) to module body 115. Note that camera lens cells 125, and fiber optic illumination bundles 95 (mounted within ferrules 130), open on the distal end of module body 115. Thus it will be seen that sealed camera module 100 comprises a module body 115 which carries image sensor assemblies 120 and ferrules 130 supporting fiber optic illumination bundles 95, and this module body 115 is secured within outer sleeve 105 and sealed with elastomer seat 110, with the electronic leads 85 of image sensor assemblies 120 and fiber optic illumination bundles 95 extending through elastomer seal 110.

Figure 4:
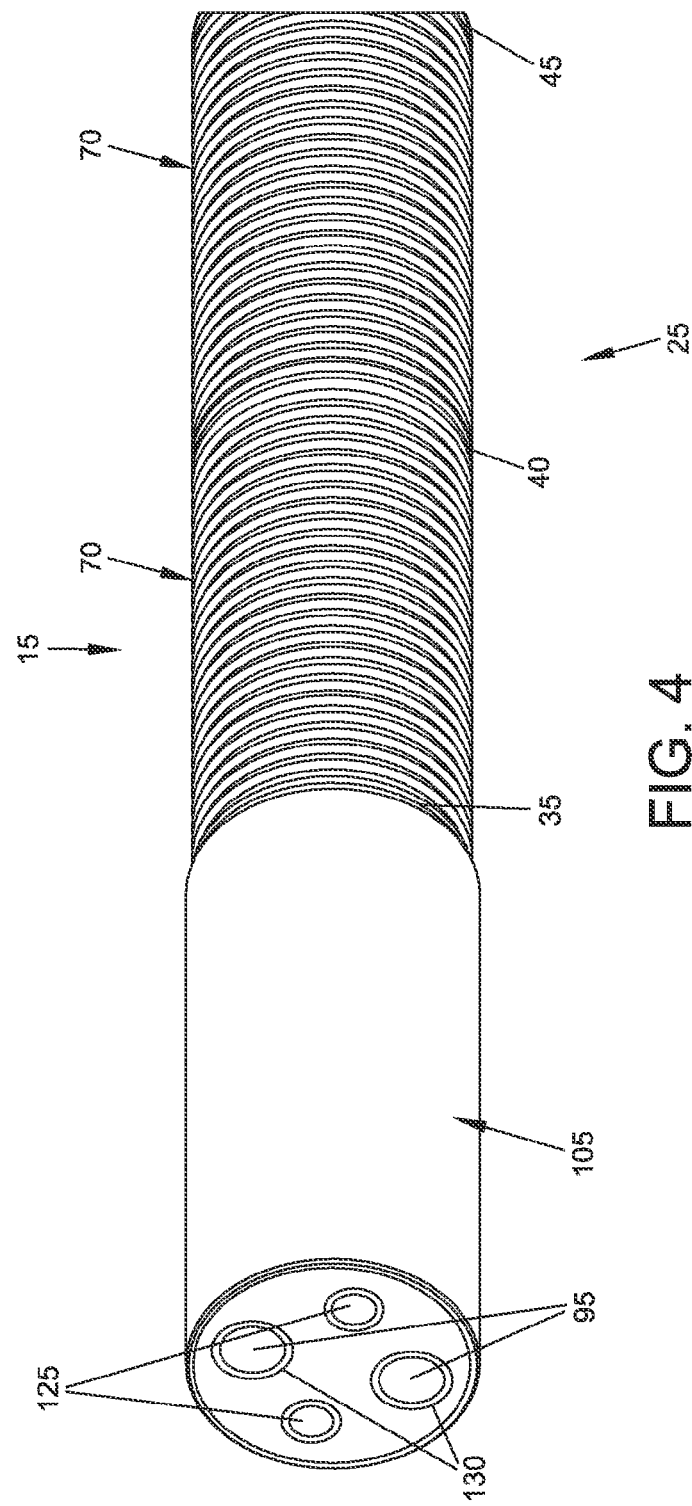
FIG. 4 is a schematic view showing the distal end of the endoscope.

FIG. 4 illustrates the assembled distal end 15 of endoscope 5, including articulating region 25. Note that the distal end of distal joiner deck 35 is received within outer sleeve 105 of sealed camera module 100, with the distal end of distal joiner deck 35 abutting elastomer seal 110 and with the outer sleeve 105 of sealed camera module 100 being hermetically bonded to the outside diameter of distal joiner deck 35. Note also that electronic leads 85 of image sensor assemblies 120 and fiber optic illumination bundles 95 extend through decks 35, 40 and 45, with metal bellows 70 cooperating with decks 35, 40 and 45 so as to render the distal end of shaft 10 hermetically sealed.

Figure 5:
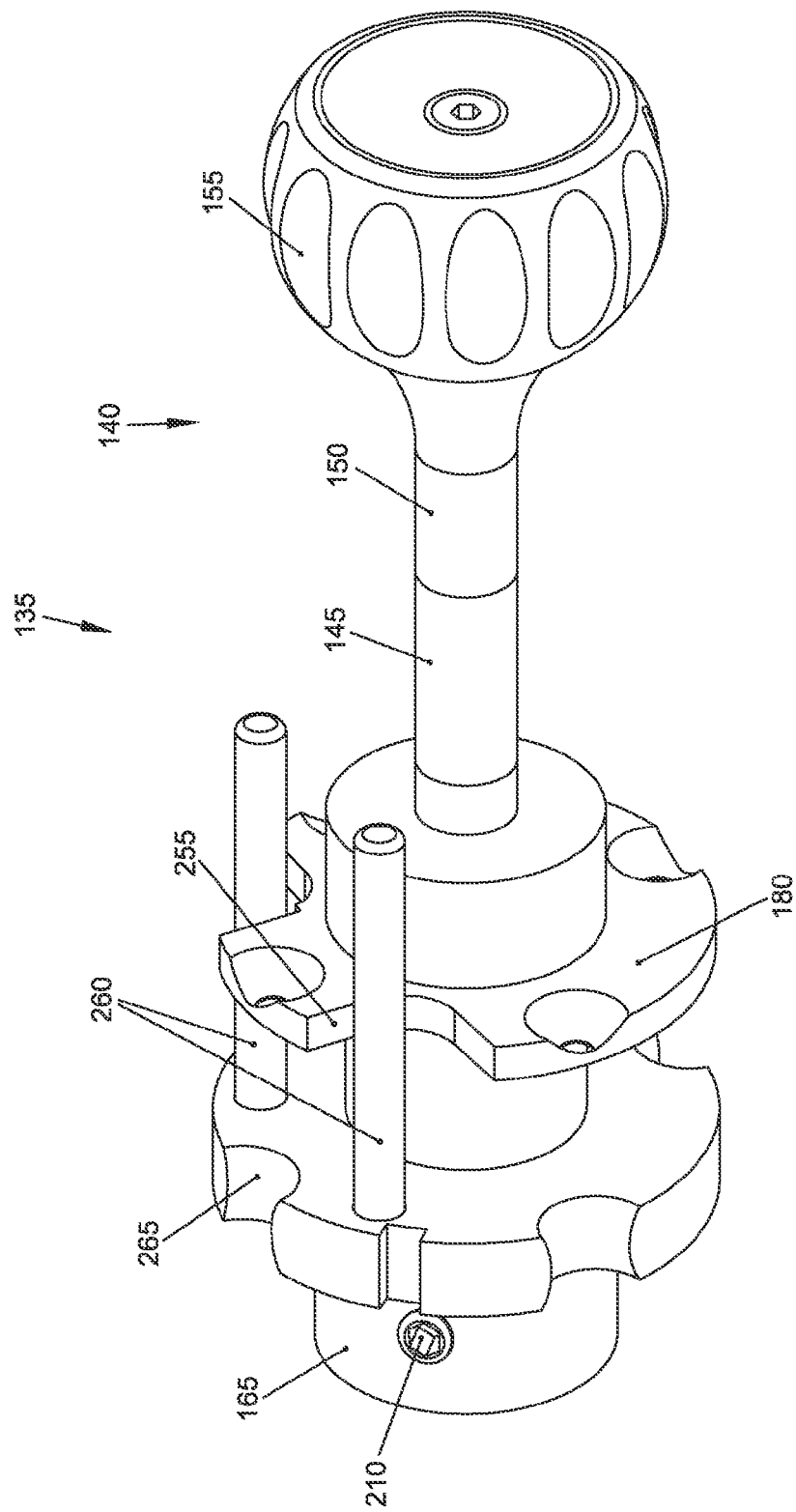

FIG. 5 shows the endoscope's steering and brake assembly 135 which is contained within, and extends out of, handle 30. Using steering and brake assembly 135, the user may direct the viewing angle of the endoscope by manipulating the control joystick 140, which comprises shaft members 145 and 150 and knob 155. The control joystick position also provides an external indication of the endoscope's viewing position, with the shaft (145, 150) of control joystick 140 representing the axis of a pointer and knob 155 representing the "tail" of the pointer.

Control joystick 140 is secured by a captive ball joint 160 (FIG. 5A) formed by a base 165, a bearing ball 170 and a braking element 175. Viewing may be directed in a 360 degree conic arc of up to, but not limited to, an included angle of 140 degrees without altering the disposition of the main body of endoscope 5 itself. FIG. 1 shows the actual device with the viewing angle being held in place by the brake feature.

Manipulating control joystick 140 deflects the distal end of the endoscope, whereby to appropriately direct its camera, by pulling one or more of the four actuating wires 60 (FIG. 5D) held in position within a swash plate 180 by four ball-ended terminations 185 (FIGS. 5D and 5E) bonded or swaged to their respective Nitinol pull wires 60.

Figure 5A:
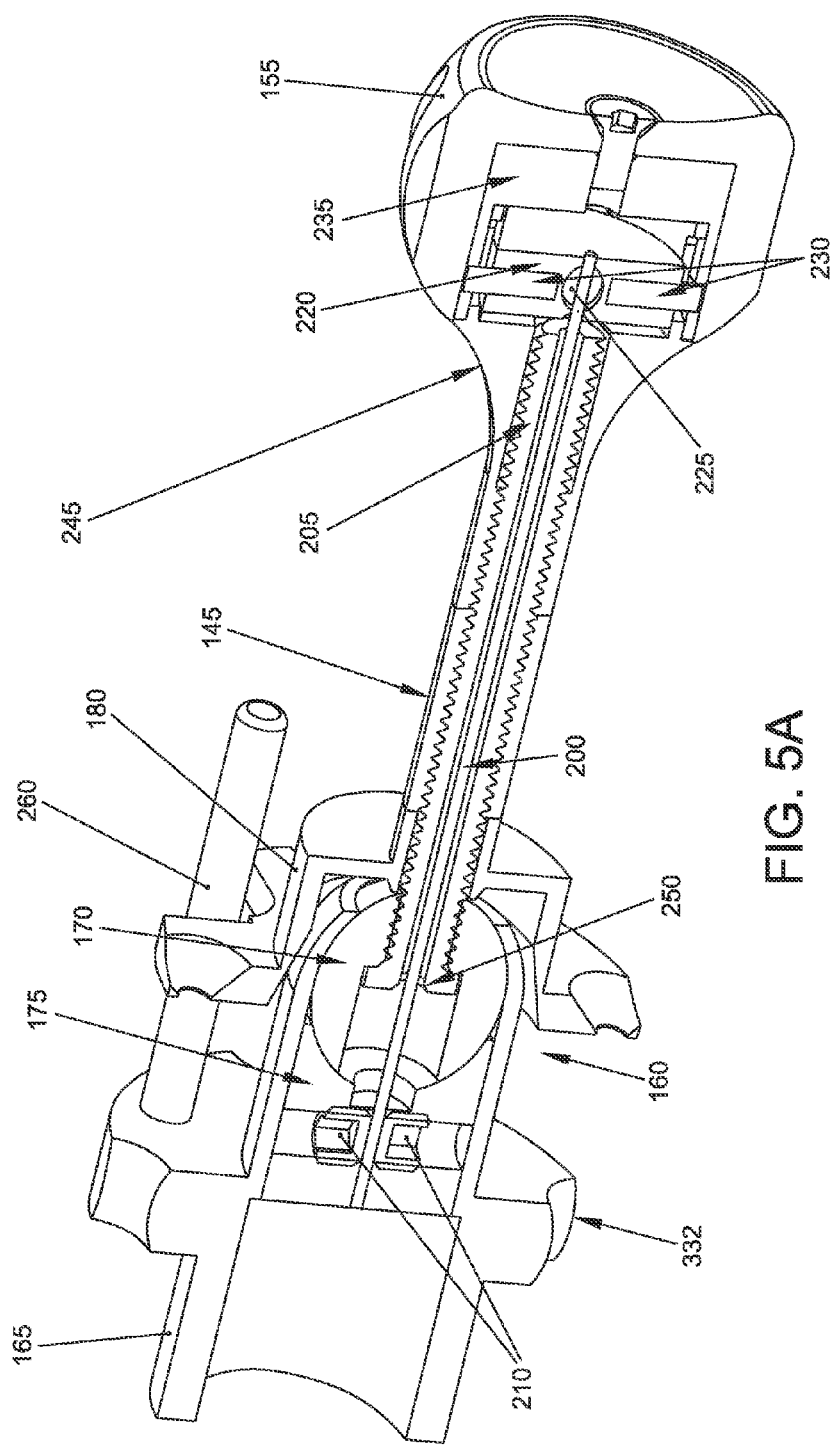
Figure 5B:
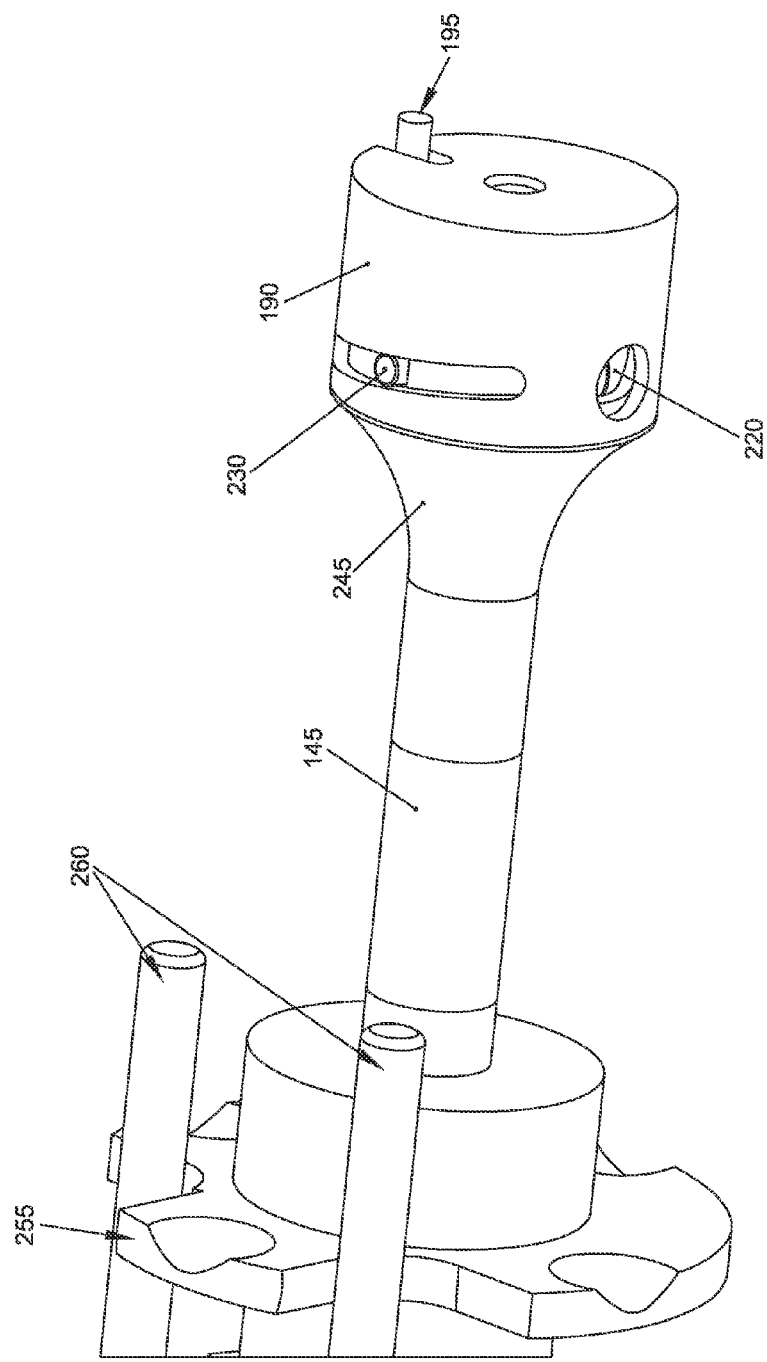
Figure 5E:
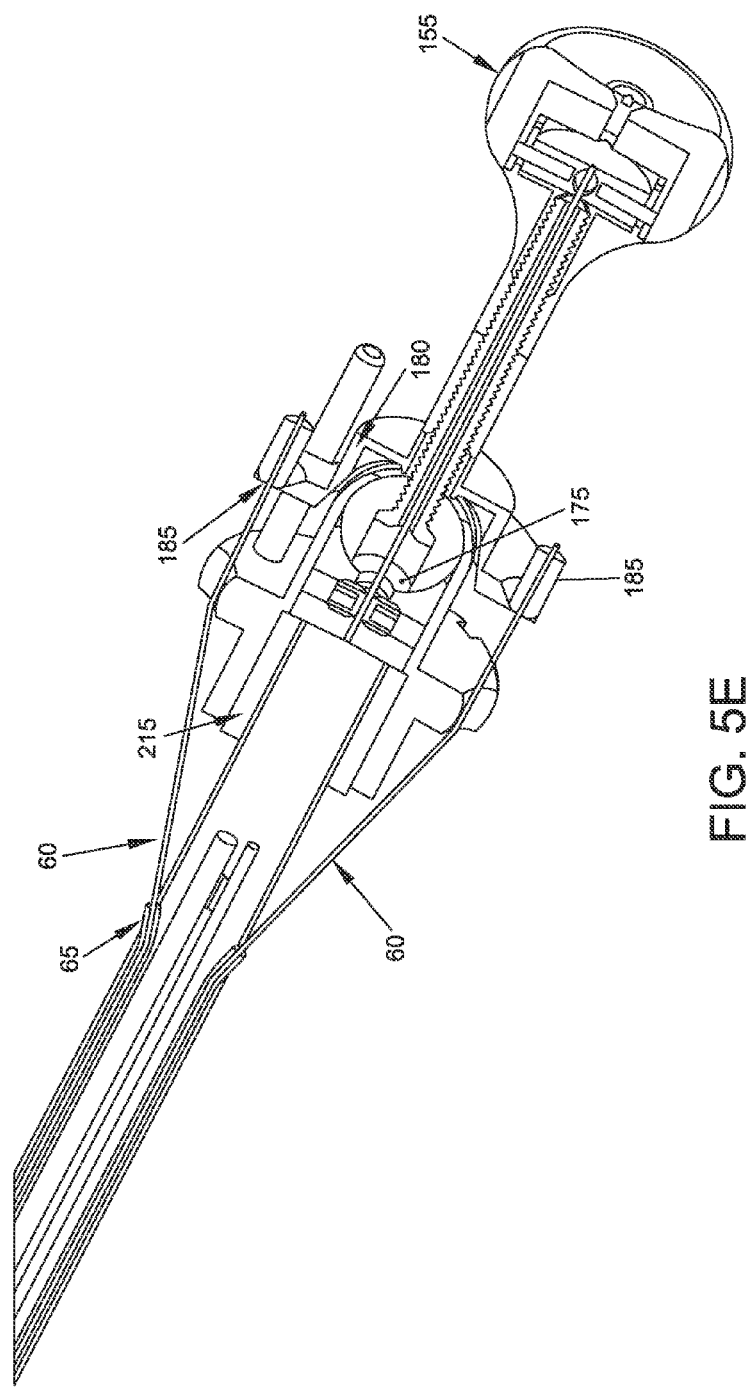

FIGS. 5A and 5E represent sectional views of the steering and brake assembly 135. When the desired view position is achieved, the brake is applied by rotating knob 155 clockwise.

Knob 155 drives the brake cam 190 (FIG. 5B) through a drive pin 195. A Nitinol brake pull wire 200 (FIG. 5A) passes through a threaded tubular control joystick core 205 and is fixed within the braking element 175 by two non-scoring set screws 210 (FIG. 5A). Nitinol (a superelastic nickel titanium alloy) is used for its high strength in brake pull wire 200 as well as in the aforementioned Nitinol superelastic wire 50 disposed within the distal end of the endoscope (see above). Nitinol's unique elastic properties resist fatigue and contribute to maintaining straightness when the brake is not engaged.

Braking element 175 (FIG. 5E) features a partial precision hemispherical socket covering approximately one third of the control stick precision bearing ball 170 (FIG. 5A). With the brake released, the braking element 175 serves as the distal element of the control stick bearing socket. The movable braking element 175 (FIG. 5A) is constrained by the main tube sleeve 215 (FIG. 5E). Proximally, the Nitinol brake pull wire 200 (FIG. 5A) is attached to the cam follower body 220 (FIG. 5A) by two non-scoring set screws 225 (only one of which is shown in FIG. 5A). Two cam follower pins 230 (FIG. 5A) are inserted through slots in the cam 235 (FIG. 5A) and restraining grooves 240 in the knob body 245 (FIG. 5C).

FIG. 5A shows, at 250, the exit point of the hole through the threaded core 205 of control joystick 140 located at the center point of the bearing ball 170. This is done to minimize any effective length change caused by the excursion made by the control joystick during use. Minimizing this length change effect removes unwanted friction and/or, conversely, sudden accidental brake release.

Referring to FIG. 5A, it will be seen that rotating the knob 155 clockwise will place increasing tension on the braking element 175 via brake pull wire 200, which in turn clamps upon the control stick bearing ball 170 with sufficient friction to effectively hold swash plate 180, and hence the distal end of the endoscope's shaft, with the desired view orientation, yet light enough to allow overriding movement of the control joystick.

Undesirable rotation of the swash plate 180 is prohibited by a restraining tab 255 (FIGS. 5A and 5B) which is disposed within a parallel pair of dowel pins 260 joined to base 165.

As shown in FIGS. 5D and 5E, the effective leverage of the swash plate 180 when acting upon the pull wires 60 is maintained by the four rounded grooves 265 in base 165.

Figure 6:
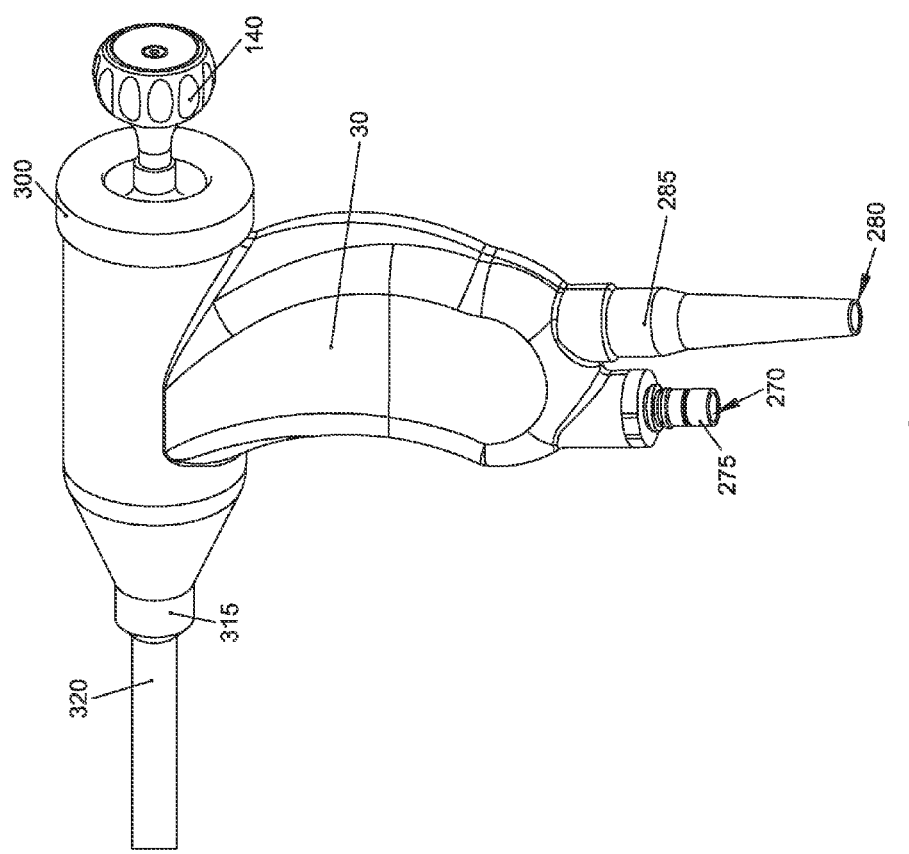
FIGS. 6 and 6A are schematic views showing the endoscope's handle and details thereof.
Figure 6A:
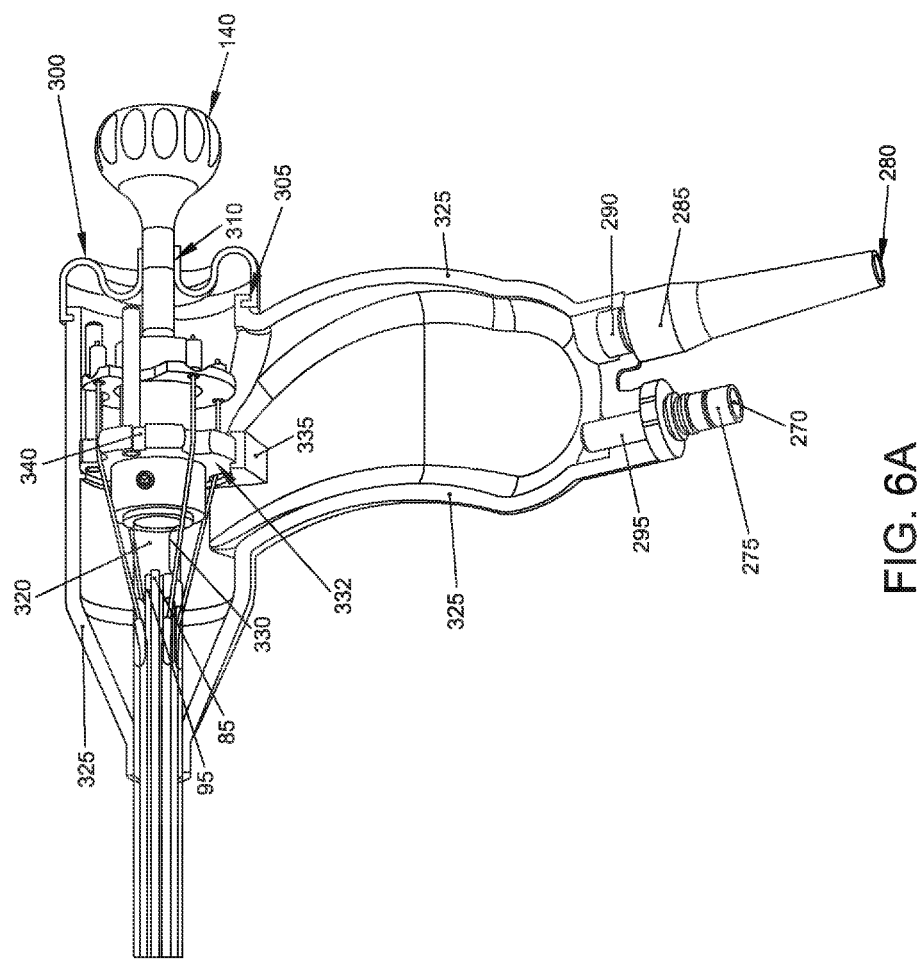

FIGS. 6 and 6A show the proximal hand control end of endoscope 5. Handle 30 may be gripped by the user and the control joystick 140 operated with the thumb of the gripping hand of the user, or the control joystick 140 may be operated with the other hand of the user.

The fiber optic illumination bundles 95 are terminated and polished at 270 in an input connector 275 to which an input light guide (not shown) from the accessory light source (not shown) is connected. The electronic leads (cable) 85 (FIG. 3) connect the image sensor assemblies 120 (FIG. 3C) to the main 3D video control unit (not shown) and are routed through (at 280) a suitable strain relief 285.

Both the electronic cable strain relief 285 and the fiber optic input connector 275 are sealably bonded at 290, 295, respectively, to handle 30. Control joystick 140 is movably sealed to handle 30 by an elastomer seal 300 which is configured so as to minimize resistance to movement of control joystick 140. Area 305 of elastomer seal 300 is preferably made slightly undersized so as to grasp and seal to handle 30, and area 310 of elastomer seal 300 is preferably made slightly undersized so as to grasp and seal to control joystick 140. This sealing may be further augmented by adding compression collars and/or suitable adhesives to areas 305, 310.

A stainless steel collar 315 provides additional support for the main tube 320 of shaft 10 where main tube 320 emerges from handle 30. Note that main tube 320 of shaft 10 is bonded and sealed to handle 30.

Handle 30 may be formed from two halves which are united during manufacturing, e.g., by bonding at 325. FIG. 6A shows the proximal portion of endoscope 5 as it appears with the left side of handle 30 removed. The fiber optic illumination bundles 95 pass through the elongated hole 330 in outer tube 320 and then extend down to input connector 275. The shielded electronic leads 85 from the image sensor assemblies 120 also pass through the elongated hole 330 in outer tube 320 and then extend down to suitable strain relief 285. The flange 332 (FIGS. 5A and 6A) of base 165 is retained and supported within matching receiving features 335 within each handle half. Unwanted rotation of the steering mechanism is prevented by two opposing machined slots 340 formed in flange 332 and fitting over mating tabs (not shown) formed in receiving features 335. The halves of handle 30 are sealed at all of the mating edge surfaces (e.g., at 325).

Thus it will be seen that shaft 10 of endoscope 5 comprises a sealed camera module 100 (FIG. 3) which has its distal working components (e.g., the image-forming optics and electronics shown in FIGS. 3A, 3B and 3C) disposed within outer sleeve 105 so as to present its objective lens cells 125 and the distal ends of its fiber optic illumination bundles 95 to the region distal to outer sleeve 105, with fiber optic illumination bundles 95 and electronic leads 85 extending proximally therefrom. Shaft 10 further comprises three decks 35, 40 and 45 (FIGS. 2 and 2A) which are connected together by an interior wire spine 50 and exterior metal bellows 70 so as to provide an articulating region to the shaft. Wire spine 50 further comprises a plurality of stacked spacer elements (e.g., rings) 55 coaxially mounted on the wire spine 50 so as to ensure consistent shaft length when the shaft is articulated.

Distal deck 35 is received within and mated to outer sleeve 105 of sealed camera module 100, and main tube 320 of shaft 10 extends proximally from proximal deck 45. The proximal end of main tube 320 is secured to handle 30. Actuating wires 60 are provided to articulate the distal end of shaft 10 and, to this end, the distal end of articulating wires 60 are secured to distal deck 35 and extend proximally along the shaft, terminating at swash plate 180 of the steering and brake assembly 135. The disposition of swash plate 180, and hence the disposition of the distal end of shaft 10, is adjusted by manipulating knob 155 at the proximal end of steering and brake assembly 135. The disposition of swash plate 180, and hence the view position of the distal end of the shaft, is adjusted by moving control joystick 140, and is locked in position by turning knob 155 of control joystick 140, which applies a proximal force to brake pull wire 200, which causes brake 175 to lock bearing ball 170 in position, whereby to lock swash plate 180 (and hence the distal end of the shaft) in position.

Other Embodiments

As shown, endoscope 5 is hand-operated. However, by linking at least two electromechanical, remotely-operated servos to at least two quadrants of the swash plate 180 and replacing handle 30 with a suitable adapter, steerable electronic stereoscopic endoscope 5 may be adapted for utilization with remotely-operated surgical robot systems.

It is well known in the art that endoscopes capable of withstanding multiple autoclave cycles must be sealed in such a way that all image-forming optics and electronics (e.g., the image sensor assemblies) are hermetically sealed by means of welding, high temperature soldering, brazing or other types of "hard" sealing methods, as opposed to elastomer seals or adhesives that are permeable to hot steam. Even very small amounts of moisture, if present in the optical path from the distal tip to the image sensor, will cause condensation and render the image unusable. The present invention lends itself to a complete hermetically-sealed autoclavable design. As seen in FIGS. 2 and 2A, the steerable distal portion of the endoscope comprises metal bellows 70 soldered or welded to the metal decks 35, 40 and 45. Typically, prior art flexible or distally-steerable endoscopes include plastic steerable outer sheath portions that preclude attaining a fully autoclavable design. Referring back to FIG. 3C, objective lens cells 125 may be designed in such a way that the distal optical lens or window is fabricated out of optical grade sapphire and soldered to the metal barrel of the lens cell. Note that this type of sapphire-to-metal sealing technology is well known in the art. The metal barrels of the camera lens cells 125 may then be welded to the module body 115 (FIG. 3B). Alternatively the front lens of each objective lens assembly 125 may be soldered directly to the module body 115. Similarly, thin sapphire windows may be soldered to the module body 115 at the distal ports of illumination fibers 95, thereby providing for autoclavable hermetic seals at the distal surface of module body 115. The outer sleeve 105 (FIG. 3) may be welded or brazed to module body 115 at its distal end. Referring to FIG. 3, elastomer seal 110 may be replaced with a metal part welded or brazed to outer sleeve 105 and having hermetic feed-through connections for illumination fiber bundles 95 and image sensor cables 85. Such hermetic feed-through connectors are known in the art. The modifications described above will encapsulate the most critical distal portion of the endoscope, which contains the optics and image sensors, into a fully hermetic assembly amenable to multiple autoclave cycles. The remaining portions of the endoscope are much less critical for small amounts of moisture and may be sealed by conventional sealing methods using elastomers and adhesives.

Figure 7A:
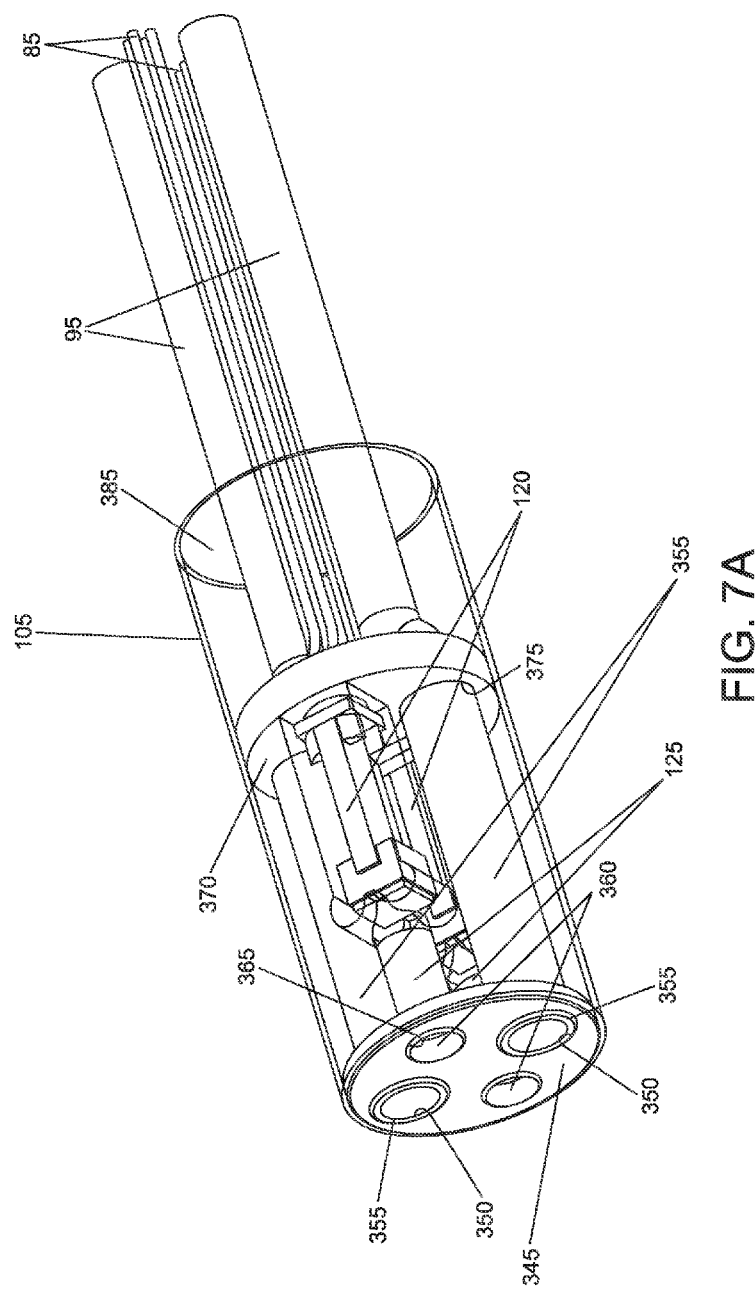
FIGS. 7A and 7B are schematic views showing an alternative configuration of the endoscope's camera head featuring improved resistance to degradation from steam autoclave sterilization.
Figure 7B:
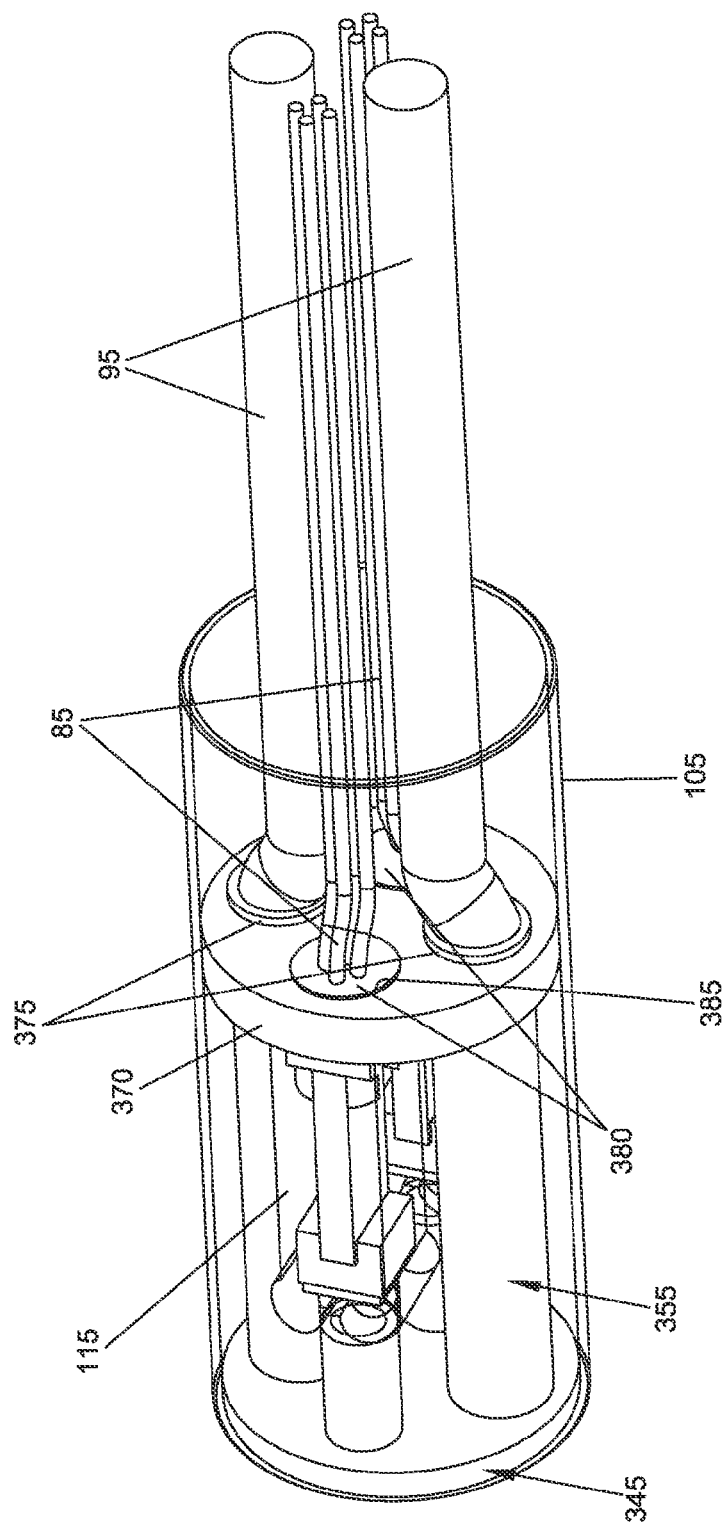

Thus, for example, FIGS. 7A and 7B show an alternative configuration of the camera head featuring improved resistance to degradation from steam autoclave sterilization. More particularly, a distal stainless steel face (or deck) 345 features two holes 350 closely fitted with the conduit tubes 355 of illumination fibers 95. Conduit tubes 355 are sealably soldered about their distal perimeter to each hole 350. Also shown are two sapphire optical windows 360 with metalized edges which are also sealably soldered in holes 365 in stainless steel face 345. These sapphire windows 360 are aligned with the optical axis of the two camera lens cells 125. A second stainless steel face (or deck) 370 constrains the proximal ends of the conduit tubes 355 of illumination fiber optics 95, i.e., conduit tubes 355 are sealably soldered in holes 375 in metal deck 370. The camera heads 120, and their corresponding lens cells 125, are constrained and held in proper alignment within module body 115 (shown transparent in FIGS. 7A and 7B). This assembled camera module is adhesively bonded within the inner diameter of the outer sleeve 105. In addition to having the illumination fiber optic conduits sealably soldered, deck 370 also has two glass-to-metal sealed headers 380 (FIG. 7B) sealably soldered within holes 385 formed in deck 370. The electronic leads 85 from the two image sensor assemblies 120 are conductively joined to the glass-sealed feed-through leads within the two glass-to-metal sealed headers 380. The two illumination fiber bundles 95 are seen exiting their corresponding sealed conduits 355 in FIG. 7B. The two decks 345, 370 are sealably soldered within the inner diameter 385 of outer sleeve 105, resulting in an assembly sealed by solder about the perimeters of the fiber optic conduits 355, sapphire windows 360 and glass headers 380.

FIGS. 6 and 6A show two connections, i.e., connection 275 for the illumination fibers 95 and connection 285 for electrical cable 85. In an alternative embodiment, these two connectors may be combined into one universal cable carrying both illumination fibers and electrical wires, and may be permanently affixed to handle 30. The proximal end of such a universal cable connects to a universal control unit (not shown) comprising a light source and the camera processor. Alternatively, such a universal cable may be detachably connected to handle 30.

In another embodiment of the present invention, rather than connecting the illumination fiber bundles 95 to an external light source via connector 275 (FIG. 6), the proximal portion of the endoscope (e.g. handle 30) may contain an illumination engine based on white LEDs optically coupled to illumination fiber bundles 95 (FIG. 3). As a result, an external light source will be no longer needed. The electrical power and control signals for the LEDs may be supplied via connector 285. Alternatively, miniature white LEDs may be disposed at the distal end of the shaft of the endoscope, thereby eliminating illumination fiber bundles 95 altogether, or coupled to very short segments of illumination fiber.

In yet another embodiment of the present invention, the proximal portion of the endoscope contains a portable electrical power supply (e.g., a battery) and a wireless transceiver for providing a wireless video link to a corresponding transceiver in the external camera control unit. Thus, electrical cable connector 285 (FIG. 6) may be eliminated. This embodiment, combined with the one described above in which LEDs are used for illumination, will render the endoscope completely untethered, thereby significantly improving user interface and freedom of movement for the operator of the device. The portable power supply (i.e., battery) will provide electrical power for image sensor assemblies, the LED light engine and the wireless video link circuitry.

In another embodiment, the proximal portion of the endoscope contains the entire video processing circuitry using highly integrated SoC ("system-on-a-chip") or CoC ("camera-on-a-chip") electronics. This embodiment, if combined with the two embodiments previously described (i.e., on-board light source, portable power supply and wireless communications), will eliminate the need for an external light source, external camera processing unit, light guide and electrical cable. The wireless video link will be established directly with a wireless device built into a video display, or with a wireless device external to, and electrically coupled to, the video display.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A steerable stereoscopic endoscope comprising:
   a shaft having a distal end, a proximal end, and an articulating region therebetween;
   stereo image acquisition means disposed at the distal end of the shaft for acquiring stereo images of a remote site;
   means for steering the portion of the shaft distal to the articulating region;
   a steering and brake assembly mounted to the proximal end of the shaft; and
   a plurality of actuating wires extending between the distal end of the shaft and the steering and brake assembly;
   wherein the steering and brake assembly comprises:
     a base having a spherical seat;
     a bearing ball rotatably mounted within the spherical seat of the base;
     a joystick core mounted to the ball;
     a swash plate mounted to the joystick core, wherein the plurality of actuating wires are attached to the swash plate;
     a brake for selectively locking the bearing ball in position within the spherical seat of the base; and
     means for actuating the brake;
     wherein the means for actuating the brake comprise a brake pull wire connected to the brake.

2. A steerable stereoscopic endoscope according to claim 1 wherein the stereo image acquisition means comprise a pair of electronic image sensor assemblies.

3. A steerable stereoscopic endoscope according to claim 1 wherein the articulating region of the shaft comprises a wire spine having a distal end and a proximal end, a distal deck mounted to the distal end of the wire spine and a proximal deck mounted to the proximal end of the wire spine.

4. A steerable stereoscopic endoscope according to claim 3 further comprising a plurality of stacked spacer elements coaxially mounted on the wire spine.

5. A steerable stereoscopic endoscope according to claim 1 further comprising fiber optic illumination bundles for delivering light to the distal end of the shaft.

6. A steerable stereoscopic endoscope according to claim 1 wherein the steering and brake assembly is mounted to the proximal end of the shaft for controlling the disposition of the portion of the shaft distal to the articulating region of the shaft.

7. A steerable endoscope according to claim 1 wherein the distal end of the shaft comprises at least two decks sealably connected by flexible metal bellows.

8. A steerable endoscope according to claim 7 further comprising a wire spine having a distal end and a proximal end, the distal end of the wire spine being mounted to a deck and the proximal end of the wire spine being mounted to a deck.

9. A steerable endoscope according to claim 8 further comprising a plurality of stacked spacer elements coaxially mounted on the wire spine.

10. A steerable endoscope according to claim 7 wherein the image acquisition means comprise a pair of electronic image sensor assemblies.

11. A steerable endoscope according to claim 7 further comprising fiber optic illumination bundles for delivering light to the distal end of the shaft.

12. A steerable endoscope according to claim 1 wherein the distal end of the shaft comprises a wire spine having a distal end and a proximal end, a first deck mounted to the distal end of the wire spine and a second deck mounted to the proximal end of the wire spine.

13. A steerable endoscope according to claim 12 further comprising a plurality of stacked spacer elements coaxially mounted on the wire spine.

14. A steerable endoscope according to claim 12 further comprising a third deck disposed intermediate the first deck and the second deck, and further wherein the third deck is slidably mounted on the wire spine.

15. A steerable endoscope according to claim 14 wherein the first deck and the third deck are sealably connected by flexible metal bellows, and further wherein the second deck and the third deck are sealably connected by flexible metal bellows.

16. A steerable endoscope according to claim 12 wherein the image acquisition means comprise a pair of electronic image sensor assemblies.

17. A steerable endoscope according to claim 12 further comprising fiber optic illumination bundles for delivering light to the distal end of the shaft.

18. A steerable endoscope according to claim 1 further comprising a knob rotatably mounted to the joystick core, with the brake pull wire being connected to the knob.

19. A steerable endoscope according to claim 18 further comprising a cam mechanism associated with the knob such that rotation of the knob results in longitudinal motion of the brake pull wire, whereby to actuate the brake.

20. A steerable endoscope according to claim 1 wherein the joystick core steers the portion of the shaft distal to the articulating region.

21. A steerable endoscope according to claim 1 wherein the brake selectively locks the disposition of the portion of the shaft distal to the articulating region of the shaft.

22. A method for acquiring an image of a remote site, the method comprising:
providing a steerable stereoscopic endoscope comprising:
a shaft having a distal end, a proximal end, and an articulating region therebetween;
stereo image acquisition means disposed at the distal end of the shaft for acquiring stereo images of a remote site;
means for steering the portion of the shaft distal to the articulating region;
a steering and brake assembly mounted to the proximal end of the shaft; and
a plurality of actuating wires extending between the distal end of the shaft and the steering and brake assembly;
wherein the steering and brake assembly comprises:
a base having a spherical seat;
a bearing ball rotatably mounted within the spherical seat of the base;
a joystick core mounted to the ball;
a swash plate mounted to the joystick core, wherein the plurality of actuating wires are attached to the swash plate;
a brake for selectively locking the bearing ball in position within the spherical seat of the base; and
means for actuating the brake;
wherein the means for actuating the brake comprise a brake pull wire connected to the brake; and
using the steerable stereoscopic endoscope to acquire an image of a remote site.

23. A method according to claim 22 wherein the distal end of the shaft comprises at least two decks sealably connected by flexible metal bellows.

24. A method according to claim 22 wherein the distal end of the shaft comprises a wire spine having a distal end and a proximal end, a first deck mounted to the distal end of the wire spine and a second deck mounted to the proximal end of the wire spine.

25. A method according to claim 22 wherein the joystick core steers the portion of the shaft distal to the articulating region.

26. A steerable endoscope according to claim 1 wherein the image acquisition means are isolated within a capsule configured to protect the image acquisition means against multiple steam autoclave cycles.

27. A steerable endoscope according to claim 26 wherein the image acquisition means comprises at least one electronic image sensor assembly.

28. A steerable endoscope according to claim 26 wherein the capsule is sealed by soldering, welding or brazing.

29. A steerable endoscope according to claim 26 wherein the capsule is sealed without the use of an adhesive or an elastomer.

30. A steerable endoscope according to claim 26 wherein the capsule comprises a metal cylinder closed off at its distal end by a distal metal deck and closed off at its proximal end by a proximal metal deck, the image acquisition means comprising at least one electronic image assembly terminating in electronic leads, with the at least one electronic image assembly being configured to image through a sapphire window sealed within the distal metal deck, and with the electrical wires from the at least one electronic image assembly passing through the proximal deck by means of a glass-to-metal sealed header.

31. A method according to claim 22 wherein the image acquisition means are isolated within a capsule configured to protect the image acquisition means against multiple steam autoclave cycles.

32. A method according to claim 31 further comprising:
subjecting the steerable endoscope to multiple steam autoclave cycles; and
using the steerable endoscope to acquire an image of a remote site.

* * * * *